US009754534B2

(12) United States Patent
Huang

(10) Patent No.: US 9,754,534 B2
(45) Date of Patent: Sep. 5, 2017

(54) CALIBRATING CIRCUIT AND CALIBRATING METHOD FOR DISPLAY PANEL

(71) Applicant: HIMAX TECHNOLOGIES LIMITED, Tainan (TW)

(72) Inventor: Hung-Yu Huang, Tainan (TW)

(73) Assignee: HIMAX TECHNOLOGIES LIMITED, Tainan (TW)

( * ) Notice: Subject to any disclaimer, the term of this patent is extended or adjusted under 35 U.S.C. 154(b) by 44 days.

(21) Appl. No.: 14/691,999

(22) Filed: Apr. 21, 2015

(65) Prior Publication Data

US 2016/0314739 A1 Oct. 27, 2016

(51) Int. Cl.

| | |
|---|---|
| ***H01L 27/14*** | (2006.01) |
| ***G09G 3/32*** | (2016.01) |
| ***A61B 8/00*** | (2006.01) |
| ***H03M 1/16*** | (2006.01) |
| ***G06F 19/22*** | (2011.01) |
| ***H04N 5/378*** | (2011.01) |
| ***H04N 5/235*** | (2006.01) |
| ***H04N 5/357*** | (2011.01) |
| ***H03F 3/00*** | (2006.01) |
| ***G09G 3/3233*** | (2016.01) |

(52) U.S. Cl.

CPC ... *G09G 3/3233* (2013.01); *G09G 2300/0842* (2013.01); *G09G 2310/0262* (2013.01); *G09G 2320/029* (2013.01); *G09G 2320/043* (2013.01)

(58) Field of Classification Search

CPC ................ G09G 3/325; G09G 3/3233; H04N 5/353–5/378

See application file for complete search history.

(56) References Cited

U.S. PATENT DOCUMENTS 8,094,218 B2 * 1/2012 Vogel .................. H04N 5/3575 348/294
2004/0036453 A1 * 2/2004 Rossi ..................... H03F 3/005 323/242

(Continued)

FOREIGN PATENT DOCUMENTS

CN 2431615 Y 5/2001
JP 2004318819 A 11/2004

(Continued)

*Primary Examiner* — Lin Li

(74) *Attorney, Agent, or Firm* — Locke Lord LLP; Tim Tingkang Xia, Esq.

(57) ABSTRACT

A circuit and a calibrating method are provided. A pixel sensor senses a terminal voltage of a driving transistor during a sensing period. A calibration sensor senses a first predetermined voltage and a second predetermined voltage during a calibration period. An amplifying circuit amplifies the terminal voltage according to a gain, and amplifies the first predetermined voltage and the second predetermined voltage according to the gain. An analog to digital converter converts the amplified terminal voltage into a digital code, and converts the amplified first predetermined voltage into a first digital code and converts the amplified second predetermined voltage into a second digital code. A gain adjusting circuit adjusts the gain according to the first digital code and the second digital code. Accordingly, the gain of the amplifying circuit is calibrated.

10 Claims, 8 Drawing Sheets

(56) References Cited

U.S. PATENT DOCUMENTS

| | | | | |
|---|---|---|---|---|
| 2007/0182673 | A1* | 8/2007 | Budzelaar | G09G 3/325 345/76 |
| 2008/0068359 | A1 | 3/2008 | Yoshida et al. | |
| 2009/0322911 | A1* | 12/2009 | Blanquart | H04N 5/2351 348/241 |
| 2009/0322912 | A1* | 12/2009 | Blanquart | H04N 5/2351 348/241 |
| 2010/0277400 | A1* | 11/2010 | Jeong | G09G 3/3275 345/76 |
| 2011/0157439 | A1* | 6/2011 | Sawada | H03M 1/164 348/300 |
| 2012/0212657 | A1* | 8/2012 | Mo | H04N 5/378 348/300 |
| 2012/0265474 | A1* | 10/2012 | Rearick | G06F 19/22 702/104 |
| 2013/0012263 | A1* | 1/2013 | Goto | H01L 27/1461 455/556.1 |
| 2015/0374335 | A1* | 12/2015 | Brown | A61B 8/4494 600/447 |

FOREIGN PATENT DOCUMENTS

| | | | |
|---|---|---|---|
| JP | 2008287119 | A | 11/2008 |
| TW | 200424995 | A | 11/2004 |
| TW | 200509025 | | 3/2005 |

* cited by examiner

CALIBRATING CIRCUIT AND CALIBRATING METHOD FOR DISPLAY PANEL

BACKGROUND

Field of Invention

The present invention relates to a calibrating circuit. More particularly, the present invention relates to a calibrating circuit and a calibrating method for a display panel.

Description of Related Art

FIG. 1 is a circuit diagram illustrating an active matrix organic light emitting diode (AMOLED) display in the prior art. The AMOLED display includes a gate driver 110, a source driver 120 and a display panel 130. The display panel 130 includes scan lines (e.g. a scan line S_1 and a scan line S_2), data lines (e.g. a data line D_1 and a data line D_2) and pixel circuits (e.g. a pixel circuit 131). The pixel circuit 131 includes a switch 132, a driving transistor 133 and an organic LED (OLED) 134.

The gate driver 110 sequentially scans scan lines of the display panel 130, so that the source driver 120 can write data voltages into the pixel circuits. Take the pixel circuit 131 as an example, during a period that the gate driver 110 turns on the switch 132 through the scan line S_1, the source driver 120 transmits a data voltage to the gate of the driving transistor 133 through the data line D_1 and the switch 132. The gate voltage of the driving transistor 133 determines a current I1 of the driving transistor 133. The current I1 flowing through the OLED 134 determines brightness of the OLED 134. The relationship formula between the gate-source voltage of the driving transistor 133 and the current I1 is written as I1=k(VGS−Vt)2, where k denotes a real number, VGS denotes the gate-source voltage of the driving transistor 133, and Vt denotes the threshold voltage of the driving transistor 133. Different driving transistors may have different threshold voltages because a process drift or other factors. The difference between the threshold voltages may cause mura (i.e. uneven brightness) or other defects. If the threshold voltage of the driving transistor 133 is sensed, then the source driver 120 can adjust the data voltage written into pixel circuit 131 to compensate the drift of the threshold voltage.

In general, a compensation circuit is disposed outside the display panel 130 to sense the threshold voltage of the driving transistor 133. The sensed threshold voltage is transmitted through an amplifier and an analog to digital converter (ADC) to obtain a digital code which is used to calibrate the threshold voltage. However, different amplifiers may have different gains due to a process drift or other factors.

SUMMARY

Embodiments of the invention provide a calibrating circuit for a display panel. The display panel includes a pixel circuit including a driving transistor. The calibrating circuit includes a pixel sensor, at least one calibration sensor, an amplifying circuit, an analog to digital converter and a gain adjusting circuit. The pixel sensor has an input terminal coupled to the pixel circuit through a data line of the display panel for sensing a terminal voltage of the driving transistor during a sensing period. The calibration sensor has input terminals coupled to a first predetermined voltage and a second predetermined voltage. The amplifying circuit has an input terminal coupled to the pixel sensor and the calibration sensor for amplifying the terminal voltage according to a gain during the sensing period, and amplifying the first predetermined voltage and the second predetermined voltage according to the gain during a calibration period. The analog to digital converter has an input terminal coupled to an output terminal of the amplifying circuit for converting the amplified terminal voltage into a digital code during the sensing period. The analog to digital converter converts the amplified first predetermined voltage into a first digital code and converts the amplified second predetermined voltage into a second digital code during the calibration period. The gain adjusting circuit is coupled to an output terminal of the analog to digital converter and the amplifying circuit for adjusting the gain of the amplifying circuit according to the first digital code and the second digital code.

In an embodiment, the gain adjusting circuit includes a first register for storing the first digital code, a second register for storing the second digital code, a comparing circuit having input terminals coupled to the first register and the second register, and a controlling circuit. The comparing circuit is configured to calculate a first difference between the first digital code and the second digital code. The controlling circuit is configured to adjust the gain of the amplifying circuit according to the first difference.

In an embodiment, if the first difference is less than a predetermined threshold, the controlling circuit increases the gain of the amplifying circuit. If the first difference is greater than the predetermined threshold, the controlling circuit decreases the gain of the amplifying circuit.

In an embodiment, after the controlling circuit adjusts the gain of the amplifying circuit, the amplifying circuit amplifies the first predetermined voltage and the second predetermined voltage according to the adjusted gain. The analog to digital converter re-generates the first digital code and the second digital code. The comparing circuit calculates a second difference between the re-generated first digital code and the re-generated second digital code. If the first difference is less than the predetermined threshold and the second difference is greater than the predetermined threshold, or the first difference is greater than the predetermined threshold and the second difference is less than the predetermined threshold, the controlling circuit stops adjusting the gain of the amplifying circuit.

In an embodiment, the first predetermined voltage is essentially at 25% of an input converting range of the amplifying circuit, and the second predetermined voltage is essentially at 75% of the input converting range.

In an embodiment, the amplifying circuit includes a switch and an amplifier. The switch is coupled to the pixel sensor and the calibration sensor. The amplifier is coupled to the switch. The switch couples the pixel sensor to the amplifier during the sensing period, and couples the at least one calibration sensor to the amplifier during the calibration period. The amplifier includes the following units. A differential amplifier has a first input terminal coupled to a first output terminal of the calibration sensor, and a second input terminal coupled to a second output terminal of the calibration sensor. A first capacitor has a first terminal and a second terminal respectively coupled to the first output terminal of the calibration sensor and the first input terminal of the differential amplifier. A second capacitor has a first terminal and a second terminal respectively coupled to the second output terminal of the calibration sensor and the second input terminal of the differential amplifier. Each of third capacitance adjusting circuits includes a third capacitor and a first switch. A first terminal of each third capacitor is coupled to the first input terminal of the differential amplifier. A second terminal of each third capacitor is coupled to a first terminal of one of the first switches. A second terminal of each first switches is coupled to the first output terminal of the differential amplifier. A second switch has a first terminal and a second terminal respectively coupled to the first input terminal of the differential amplifier and the first output terminal of the differential amplifier. A third switch has a first terminal coupled to second terminals of the first switches and a second terminal coupled to a common mode voltage. A fourth switch has a first terminal coupled to the second terminal of the first switches and a second terminal coupled to the first output terminal of the differential amplifier. A fourth capacitor has a first terminal coupled to the second input terminal of the differential amplifier. A fifth switch has a first terminal and a second terminal respectively coupled to the second input terminal of the differential amplifier and the second output terminal of the differential amplifier. A sixth switch has a first terminal and a second terminal respectively coupled to a second terminal of the fourth capacitor and the common mode voltage. A seventh switch has a first terminal and a second terminal respectively coupled to the second terminal of the fourth capacitor and the second output terminal of the differential amplifier. The gain adjusting circuit controls a conducting status of each first switch to adjust the gain of the amplifying circuit.

Embodiments of the invention provide a calibrating method for the display panel. The calibrating method includes the following steps. A first predetermined voltage and a second predetermined voltage are sensed. The first predetermined voltage and the second predetermined voltage are amplified according to a gain by the amplifying circuit during a calibration period. The amplified first predetermined voltage is converted into a first digital code, and the amplified second predetermined voltage is converted into a second digital code by the analog to digital converter during the calibration period. The gain of the amplifying circuit is adjusted according to the first digital code and the second digital code.

In an embodiment, the step of adjusting the gain of the amplifying circuit according to the first digital code and the second digital code includes: calculating a first difference between the first digital code and the second digital code; if the first difference is less than a predetermined threshold, increasing the gain of the gain of the amplifying circuit; and if the first difference is greater than the predetermined threshold, decreasing the gain of the amplifying circuit.

In an embodiment, the calibrating method further includes: after adjusting the gain of the amplifying circuit, amplifying, by the amplifying circuit, the first predetermined voltage and the second predetermined voltage according to the adjusted gain, and re-generating, by the analog to digital converter, the first digital code and the second digital code; calculating a second difference between the re-generated first digital code and the re-generated second digital code; if the first difference is less than the predetermined threshold and the second difference is greater than the predetermined threshold, or the first difference is greater than the predetermined threshold and the second difference is less than the predetermined threshold, stopping adjusting the gain of the amplifying circuit.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings. In the specification and the claims, “couple” is referred as a direct or indirect connection. For example, when “a first device is coupled to a second device” is described, then it should be referred as the first device being directly connected to the second device, or the first device being indirectly connected to the second device through other devices or connection means. Moreover, the units/structure/steps having the same label represents, if possible, the identical or similar part.

Figure 1:
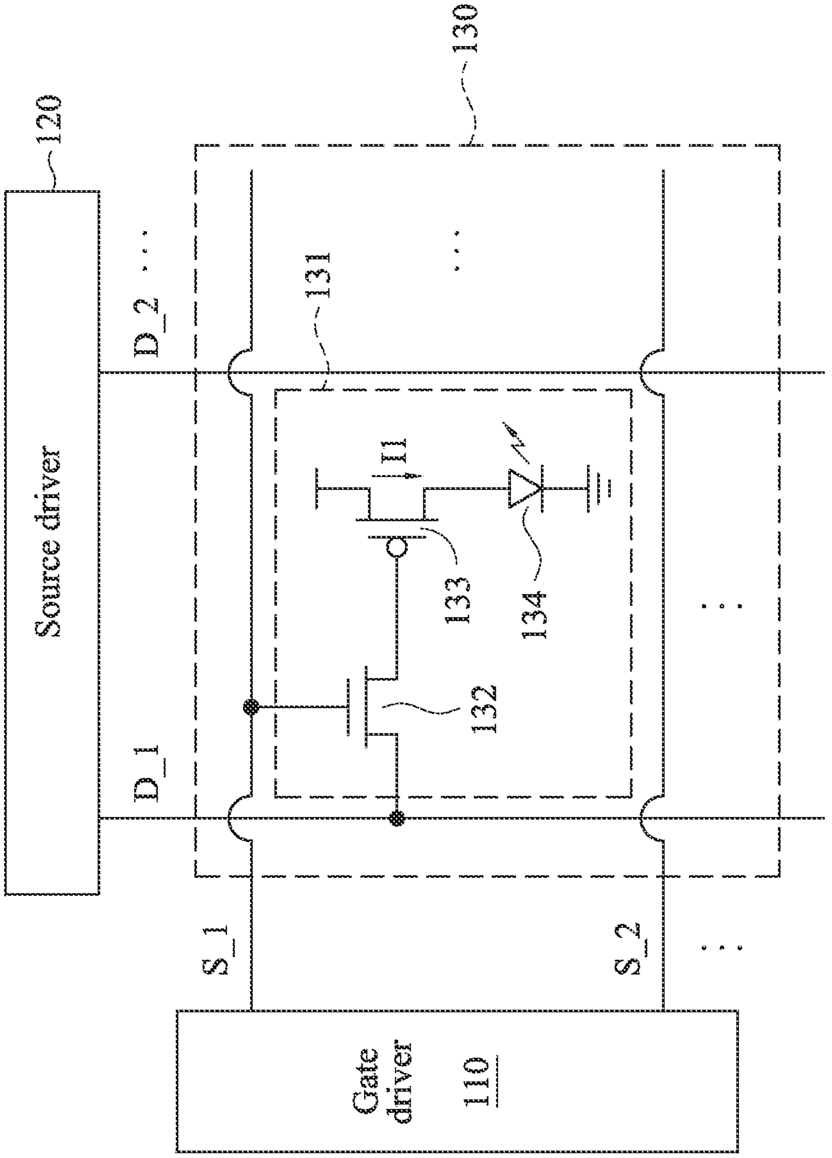
FIG. 1 (Prior Art)
FIG. 1 is a circuit diagram illustrating an active matrix organic light emitting diode (AMOLED) display in the prior art.
Figure 2:
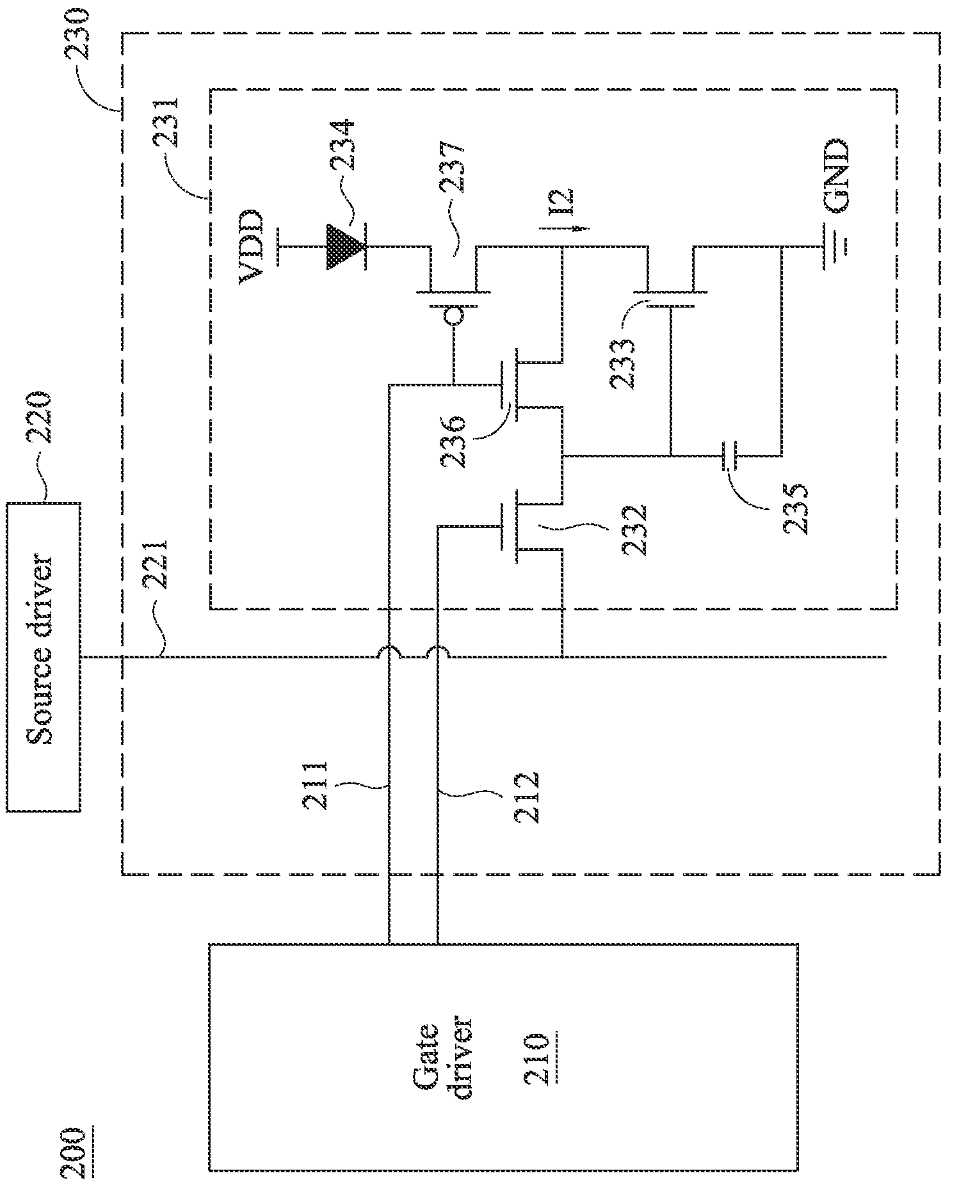
FIG. 2 is a schematic circuit diagram illustrating a display device 200 according to an embodiment.

FIG. 2 is a schematic circuit diagram illustrating a display device 200 according to an embodiment. The display device 200 includes a gate driver 210, a source driver 220 and a display panel 230. The display panel 230 includes scan lines (also referred to gate lines), data lines (also referred to source lines) and pixel circuits. Take a scan line 212, a data line 221 and a pixel circuit 231 as examples, the pixel circuit 231 includes a switch 232, a driving transistor 233, a LED 234, a storing capacitor 235, a switch 236 and a switch 237. The LED 234 may be an OLED or other types of LED.

During a scanning period, the gate driver 210 turns off the switch 236 and turns on the switch 237 through a mode line 211. During the scanning period, the gate driver 210 turns on the switch 232 through the scan line 212, so that the source driver 220 transmits a data voltage to the gate of the driving transistor 233 through the data line 221. The data voltage is stored in the storing capacitor 235. A gate voltage of the driving transistor 233 determines a current I2. The current I2 flowing through the OLED 234 determines brightness of the OLED 234.

During a sensing period, the gate driver 210 turns on the switch 236 and turns off the switch 237 through the mode line 211. During the sensing period, the gate driver 210 turns on the switch 232 through the scan line 212, so that a calibrating circuit (will be described below) in the source driver 220 senses a terminal voltage (i.e. threshold voltage in the embodiment of FIG. 2) of the driving transistor 233 through the data line 221. After the terminal voltage of the driving transistor 233 is sensed, the source driver 220 adjusts the data voltage to be written into the pixel circuit 231 to compensate the drift of the threshold voltage.

It should be noted that, the terminal voltage sensed by the source driver 220 in the embodiment of FIG. 2 is the voltage on the gate (drain) of the driving transistor 233, but the pixel circuit 231 may have another different structure in other embodiments. Therefore, the terminal voltage may also be a voltage on the source of the driving transistor 233. The structure of the pixel circuit 231 is not limited in the invention, and which terminal the terminal voltage is on is not limited, either.

Figure 3A:
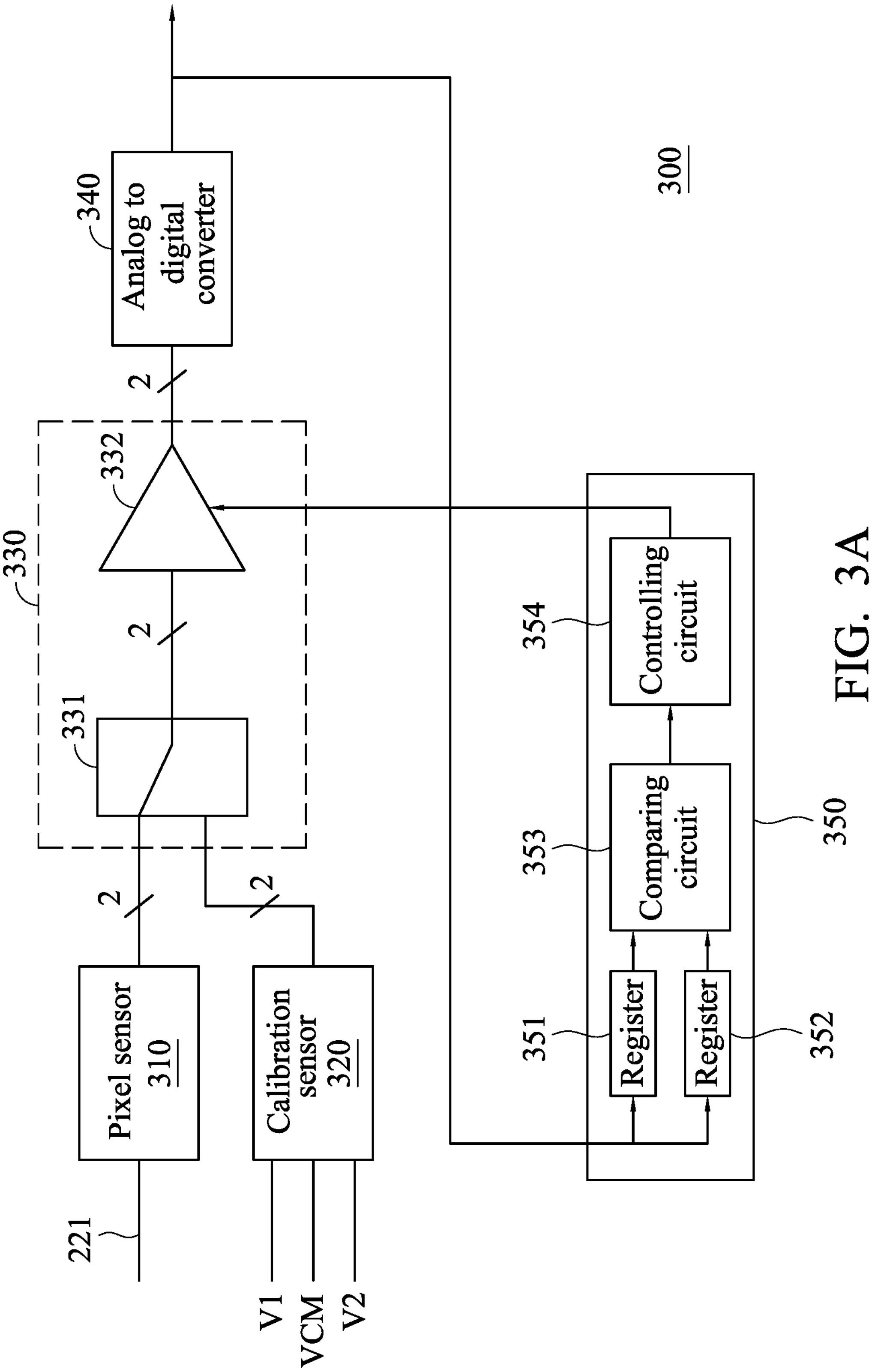
FIG. 3A is a schematic block diagram illustrating a calibrating circuit 300 during the sensing period according to an embodiment.

FIG. 3A is a schematic block diagram illustrating a calibrating circuit 300 during the sensing period according to an embodiment. Referring to FIG. 2 and FIG. 3A, the calibrating circuit 300 includes a pixel sensor 310, at least one calibration sensor 320, an amplifying circuit 330, an analog to digital converter 340 and a gain adjusting circuit 350. In the embodiment, the amplifying circuit 330 includes a switch 331 and an amplifier 332, in which the switch 331 is coupled to the pixel sensor 310 and the calibration sensor 320, and the amplifier 332 is coupled to the switch 331. The gain adjusting circuit 350 includes a first register 351, a second register 352, a comparing circuit 353 and a controlling circuit 354.

An input terminal of the pixel sensor 310 is coupled to the pixel circuit 231 through the data line 221, and input terminals of the amplifying circuit 330 are coupled to the pixel sensor 310 and the calibration sensor 320. During the sensing period (referring to FIG. 3A), the pixel sensor 310 obtains the terminal voltage of the driving transistor 232, and the switch 331 couples the pixel sensor 310 to the amplifier 332. The pixel sensor 310 transmits the terminal voltage and a common mode voltage to the amplifier 332. The amplifier 332 amplifies the terminal voltage according to a gain. Note that the gain may be greater or less than 1. In the embodiment, the gain is about 0.5, but the invention is not limited thereto. An input terminal of the analog to digital converter 340 is coupled to the amplifying circuit 330 for converting the terminal voltage into a digital code during the sensing period. The digital code is used to adjust the data voltage transmitted to the pixel circuit 231. However, the display device 300 may have multiple amplifiers 332 which may have different gains due to a process drift or other factors. The calibration sensor 320 and the gain adjusting circuit 350 can calibrate the gain of the amplifier 332.

Figure 3B:
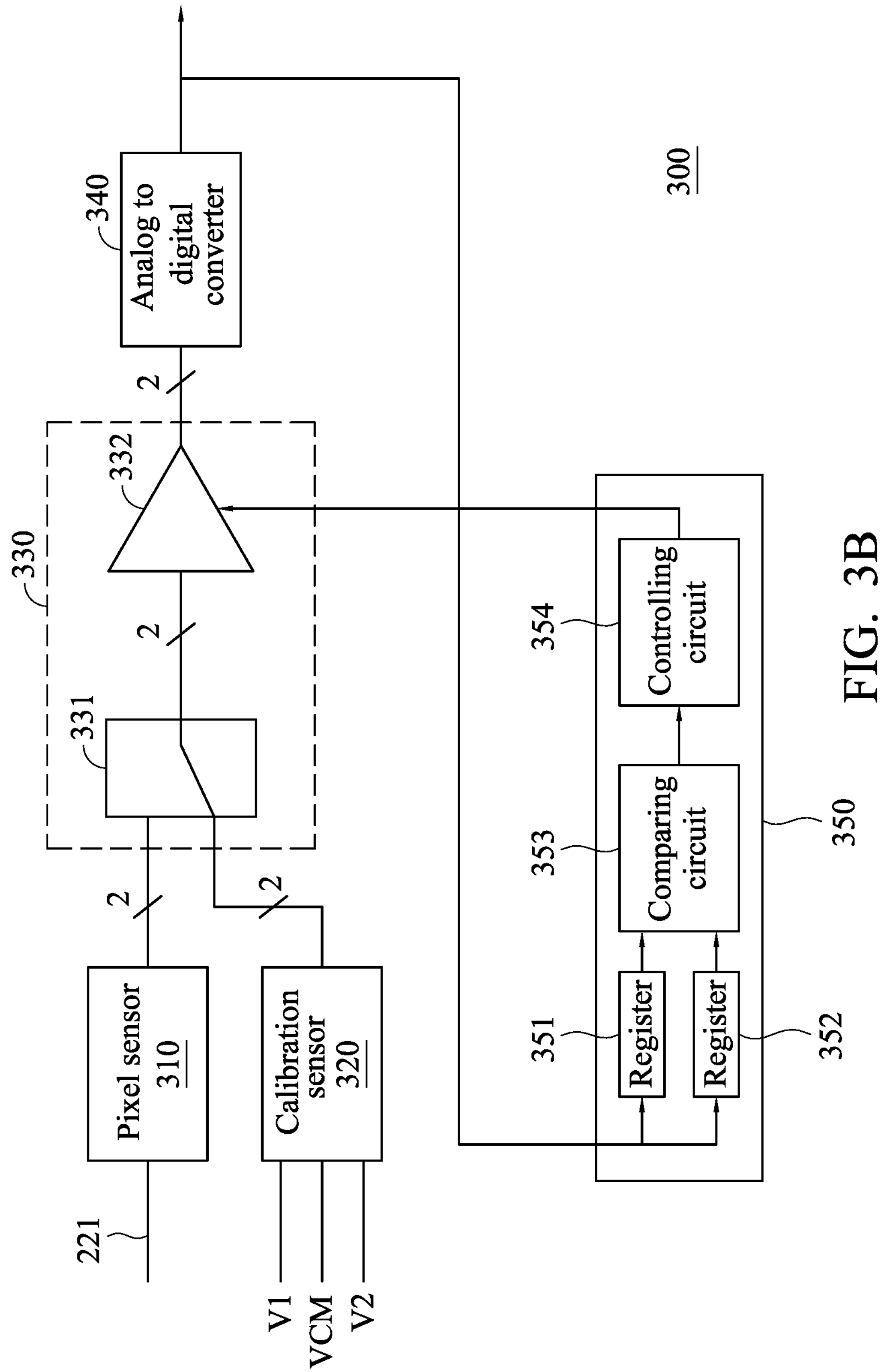
FIG. 3B is a schematic block diagram illustrating a calibrating circuit 300 during the calibration period according to an embodiment.

Input terminals of the calibration sensor 320 are coupled to a first predetermined voltage V1, a common mode voltage VCM and a second predetermined voltage V2. During the calibration period (as shown in FIG. 3B), the switch 331 couples the calibration sensor 320 to the amplifier 332, and the calibration sensor 320 sequentially transmits the first predetermined voltage V1 and second predetermined voltage V2 to the amplifier 332. In detail, the calibration sensor 320 first transmits the first predetermined voltage V1 and the common mode voltage VCM to the amplifier 332. The amplifier 332 amplifies the first predetermined voltage V1 according to its gain. Then, the analog to digital converter 340 converts the amplified first predetermined voltage V1 into a first digital code, which is stored in the first register 351. Next, the calibration sensor 320 transmits the second predetermined voltage V2 and the common mode voltage VCM to the amplifier 332, and the amplifier 332 amplifies the second predetermined voltage V2 according to its gain. The analog to digital converter 340 converts the amplified second predetermined voltage V2 into a second digital code which is stored in the second register 352.

Because the first predetermined voltage V1 and the second predetermined voltage V2 are known, and the gain of the amplifier 332 is required to be fixed at a certain value, the first digital code and the second digital code should be two particular values. Therefore, the gain adjusting circuit 350 can adjust the gain of the amplifier 332 according to the first digital code and the second digital code. In the embodiment, the comparing circuit 353 calculates a difference (referred to a first difference) between the first digital code and the second digital code, and the controlling circuit 354 adjusts the gain of the amplifier 332 according to the first difference.

Figure 4A:
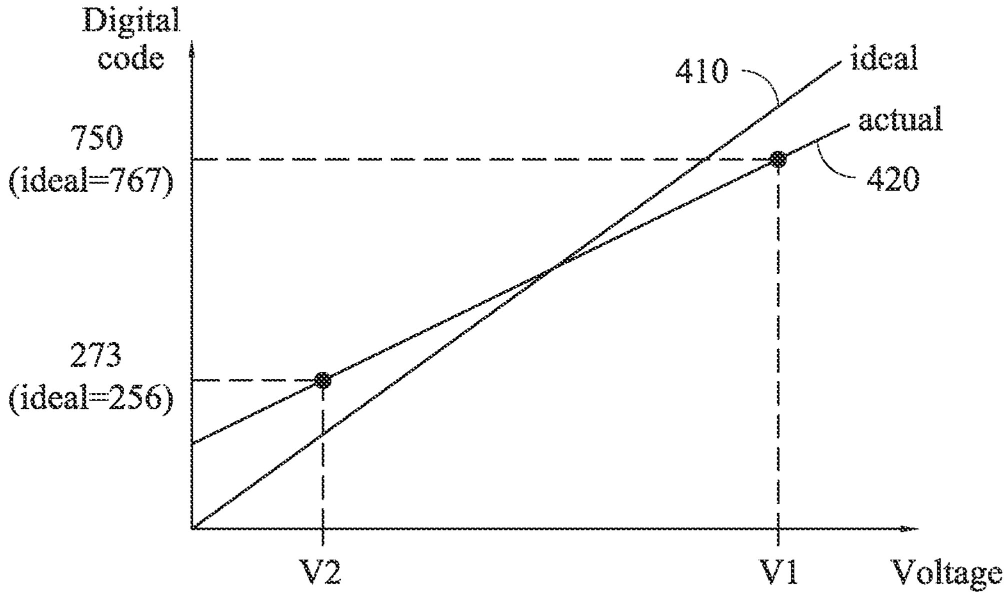
FIGS. 4A and 4B are schematic diagrams illustrating the adjustment of the gain according to the first difference in an embodiment.
Figure 4B:
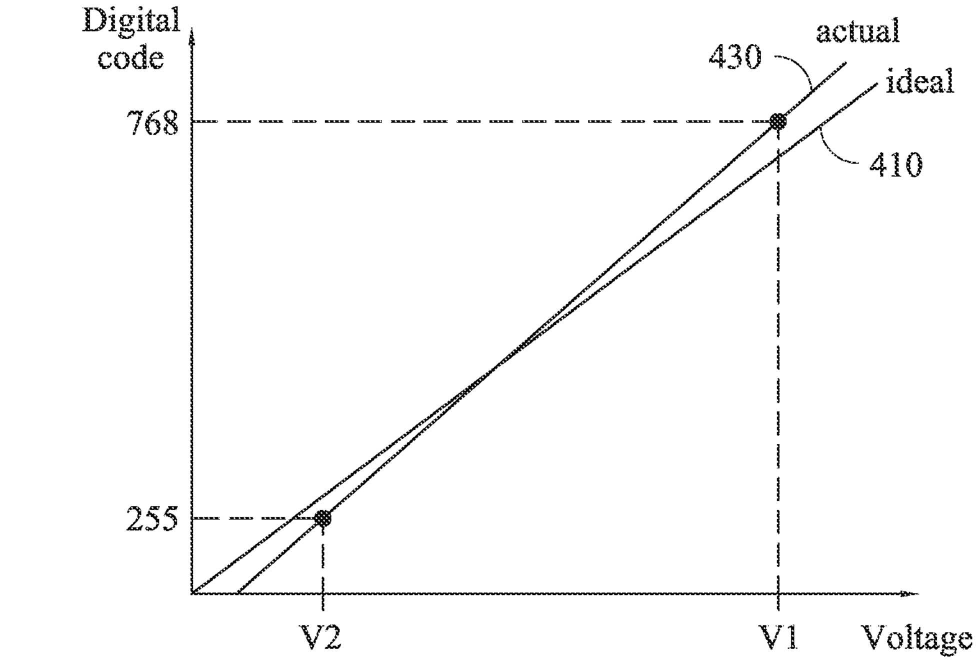

FIGS. 4A and 4B are schematic diagrams illustrating the adjustment of the gain according to the first difference in an embodiment. Referring to FIG. 4A, the horizontal axis illustrates the first predetermined voltage V1 and the second predetermined voltage V2, and the vertical axis represent the output of the analog to digital converter 340. A curve 410 represent an ideal converting curve of the amplifier 332, and a curve 420 is an actual curve. In the embodiment, the amplifier 332 has an input converting range which is, for example, 4 volts to 8 volts. The first predetermined voltage V1 is essentially at 75% of the input converting range (i.e. 7 volts), and the second predetermined voltage V2 is essentially at 25% of the input converting range (i.e. 5 volts). In addition, a digital code outputted from the analog to digital converter 340 has a resolution of 10 bits. Therefore, after the first predetermined voltage V1 and the second predetermined voltage V2 are passed through the ideal amplifier 332, the first digital code should be "767", and the second digital code should be "256". However, there is a difference between the actual curve 420 and the ideal curve 410. In the embodiment, the obtained first digital code is "750", and the second digital code is "273". The comparing circuit 353 calculates the first difference (i.e. 750−273=477) between the first digital code and the second digital code. The controlling circuit 354 determines whether the first difference is less than a predetermined threshold which is determined according to the digital codes corresponding to the ideal curve 410. In the embodiment, the predetermined threshold is 1024/2=512. If the first difference is less than the predetermined threshold, it means the gain of the amplifier 332 is too small, therefore the controlling circuit 354 increased the gain of the amplifier 332. If the first difference is greater than the predetermined threshold, it means the gain of the amplifier 332 is too large, and therefore controlling circuit 354 decreased the gain of the amplifier 332. In the embodiment of FIG. 4A, the first difference "477" is less than the predetermined threshold "512", therefore the controlling circuit 354 increases the gain of the amplifier 332. After the gain is adjusted, referring to FIG. 4B, the amplifier 332 has a curve 430 closer to the ideal curve 410 relative to the curve 420.

In the embodiment, the first predetermined voltage V1 is at 75% of the input converting range, the second predetermined voltage V2 is at 25% of the input converting range, and the predetermined threshold is "512". However, in other embodiments, the first predetermined voltage V1 and the second predetermined voltage V2 may have other values, and thus the predetermined threshold is correspondingly changed. For example, if the first predetermined voltage V1 is at 80% of the input converting range and the second predetermined voltage V2 is at 20%, then the predetermined threshold is about 614 or 615. It is worth mentioning that the first predetermined voltage V1 should not be set too large, and the second predetermined voltage V2 should not be set too small because it may not be linear at two ends of the actual curve 420. In an embodiment, the first predetermined voltage V1 is at 60%-90% of the input converting range, and the second predetermined voltage is at 10%-40% of the input converting range. In addition, if the resolution of the digital code outputted by the analog to digital converter 340 has more or less bits, the predetermined threshold is also correspondingly changed. Moreover, in the embodiment, the gain calibrating circuit 350 adjusts the gain of the amplifier 332 according to the difference between the first digital code and the second digital code, but the gain calibrating circuit 350 may adjust the gain of the amplifier 332 according to the ratio of the first digital code to second digital code in other embodiments.

Referring to FIG. 3B, in an embodiment, the controlling circuit 354 slightly adjusts the gain of the amplifier 332 each time so that the controlling circuit 354 needs to determine whether to stop or continue the adjustment. To be specific, after the gain of the amplifier 332 is adjusted according to the first difference, the first predetermined voltage V1 and the second predetermined voltage V2 are again inputted into the amplifier 332. The amplifier 332 amplifies the first predetermined voltage V1 and the second predetermined voltage V2 according to the adjusted gain, and the analog to digital converter 340 re-generates the first digital code and the second digital code. The re-generated first digital code and the re-generated second digital code are then stored in the first register 351 and the second register 352, respectively. The comparing circuit 353 calculates a difference (also referred to a second difference) between the re-generated first digital code and the re-generated second digital code. If the first difference is less than the predetermined threshold and the second difference is greater than the predetermined threshold (as shown in the embodiment of FIG. 4A and FIG. 4B), or the first difference is greater than the predetermined threshold and the second difference is less than the predetermined threshold, then the controlling circuit 354 stops the adjustment of the gain. If the first difference and the second difference are both less than the predetermined threshold or both greater than the predetermined threshold, it means there is still a gap between the gain of the amplifier 332 and the ideal gain, and thus the controlling circuit 354 continues the adjustment.

Figure 5:
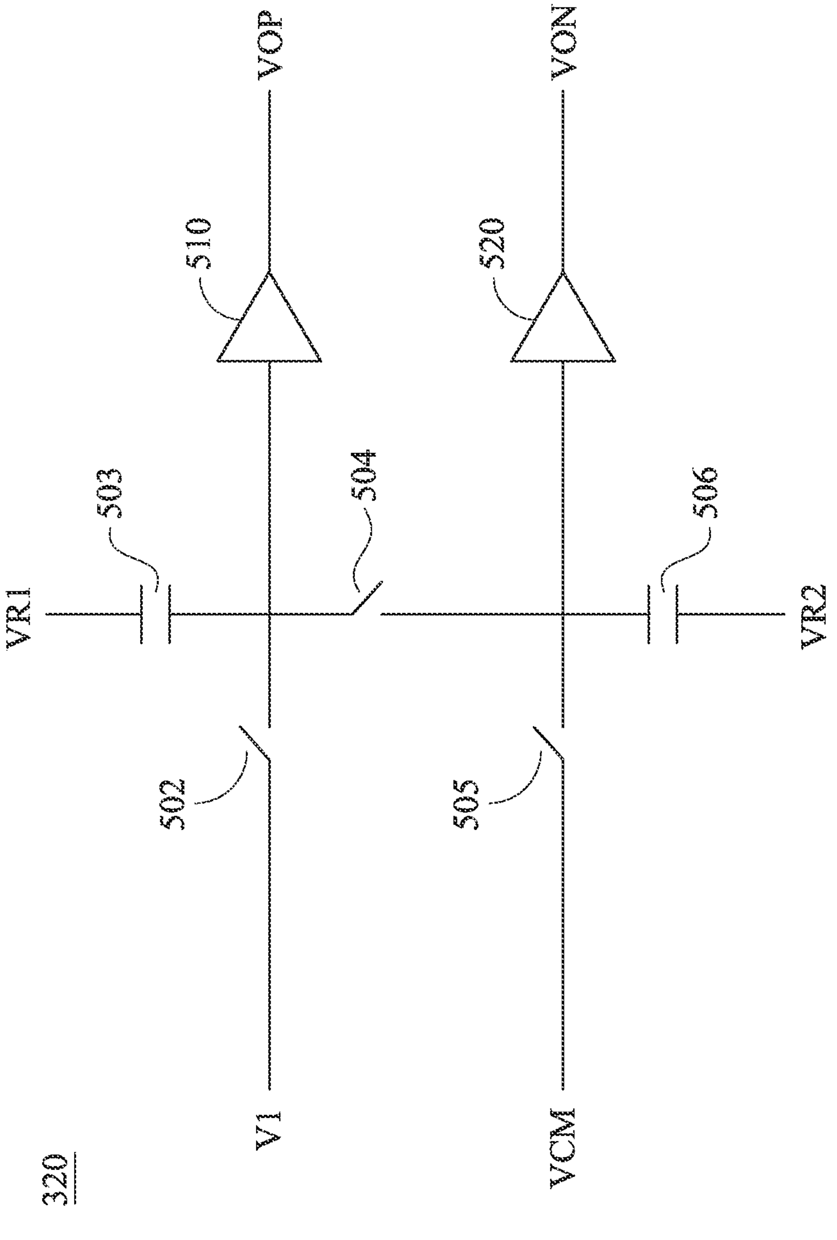
FIG. 5 is a circuit diagram illustrating the calibration sensor according to an embodiment.

FIG. 5 is a circuit diagram illustrating the calibration sensor according to an embodiment. In the embodiment, there are two calibration sensors having identical circuit structures. One of the two calibration sensors receives the first predetermined voltage V1 and the common mode voltage VCM (as illustrated in FIG. 5), and the other one receives the second predetermined voltage V2 and the common mode voltage VCM. For simplification, only the calibration sensor receiving the first predetermined voltage V1 and the common mode voltage VCM is illustrated, and the first predetermined voltage V1 can be replaced with the second predetermined voltage V2 in the other calibration sensor. Referring to FIG. 5, the calibration sensor 320 includes 502, 504 and 505, capacitors 503 and 506, and gain amplifiers 510 and 520. A first terminal of the switch 502 is coupled to the first predetermined voltage V1. A first terminal of the switch 505 is coupled to the common mode voltage VCM. A first terminal and a second terminal of the switch 504 are respectively coupled to a second terminal of the switch 502 and a second terminal of the switch 505.

A first terminal and a second terminal of the capacitor 503 are respectively coupled a first reference voltage VR1 and the second terminal of the switch 502. The first reference voltage VR1 may be any fixed voltage (e.g. system voltage, ground voltage, or another fixed voltage) with any level. A first terminal and a second terminal of the capacitor 506 are respectively coupled to a second reference voltage VR2 and the second terminal of the switch 505. The second reference voltage VR2 may be any fixed voltage (e.g. system voltage, ground voltage, or another fixed voltage) with any level. The first reference voltage VR1 may be identical to or different from the second reference voltage VR2.

An input terminal of the gain amplifier 510 is coupled to the second terminal of the switch 502, and an output terminal of the gain amplifier 510 is taken as a first output terminal VOP of the calibration sensor 320. An input terminal of the gain amplifier 520 is coupled to the second terminal of the switch 505, and an output terminal of the gain amplifier 520 is taken as a second output terminal VON of the calibration sensor 320. The gain amplifier 510 and the gain amplifier 520 may be any type of amplifying circuit. For example, in the embodiment, the gain amplifier 510 and the gain amplifier 520 are unit gain amplifiers.

When the display panel 230 is in a first period (first phase) T1 of the sensing period, the switch 502 and the switch 505 are turned on, and the switch 504 is turned off. Therefore, in the first period T1, the gain amplifier 510 outputs VOP(T1)=V1+Voffset1, and the gain amplifier 520 output VON(T1)=VCM+Voffset2, in which Voffset1 denotes a voltage offset of the gain amplifier 510, and Voffset2 denotes a voltage offset of the gain amplifier 520. The amplifier 332 calculates VOP(T1)−VON(T1)=(V1+Voffset1)−(VCM+Voffset2) during the first period T1. During a second period (second phase) T2 of the sensing period, the switch 502 and the switch 505 are turned off, and the switch 504 is turned on. During the second period T2, the gain amplifier 510 outputs VOP(T2)=Vreset+Voffset1, and the gain amplifier 520 output VON(T2)=Vreset+Voffset2, in which Vreset denotes an input terminal voltage of the gain amplifier 510 and the gain amplifier 520 when the switch 504 is turned on. The amplifier 332 calculates VOP(T2)−VON(T2)=Voffset1−Voffset2 during the second period T2. The amplifier 332 calculates [VOP(T1)−VON(T1)]−[VOP(T2)−VON(T2)]=V1−VCM. Therefore, the voltage offsets of the gain amplifier 510 and the gain amplifier 520 are eliminated.

Figure 6:
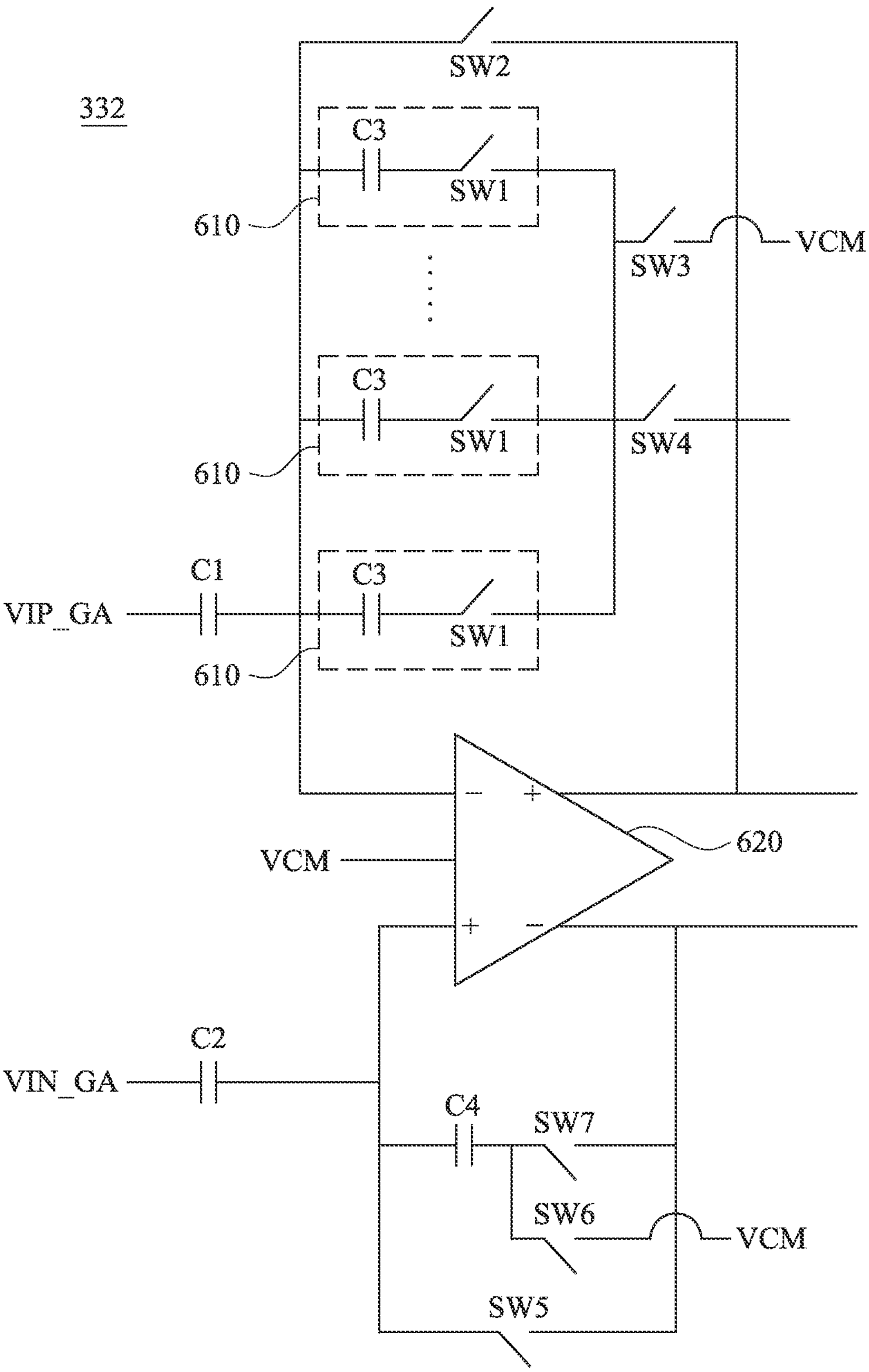
FIG. 6 is a circuit diagram illustrating the amplifier 332 according to an embodiment.

FIG. 6 is a circuit diagram illustrating the amplifier 332 according to an embodiment. Referring to FIG. 5 and FIG. 6, a first input terminal VIP_GA of the amplifier 332 is coupled to the first output terminal VOP of the calibration sensor 320, and a second input terminal VIN_GA of the amplifier 332 is coupled to the second output terminal VON of the calibration sensor 320. The amplifier 332 includes a first capacitor C1, a second capacitor C2, multiple third capacitance adjusting circuits 610, a fourth capacitor C4, a second switch SW2, a third switch SW3, a fourth switch SW4, a fifth switch SW5, a sixth switch SW6, a seventh switch SW7 and a differential amplifier 620. A first input terminal (e.g. inverting input terminal) and a second input terminal (e.g. non-inverting input terminal) of the differential amplifier 620 are respectively coupled to the first input terminal VIP_GA and the second input terminal VIN_GA of the amplifier 332.

A first terminal and a second terminal of the first capacitor C1 are respectively coupled to the first input terminal VIP_GA of the amplifier 332 and the first input terminal of the differential amplifier 620. Each third capacitance adjusting circuit 610 includes a third capacitor C3 and a first switch SW1. A first terminal of each third capacitor C3 is coupled to the first input terminal of the differential amplifier 620, and a second terminal of each third capacitor C3 is coupled to a first terminal of the first switch SW1. A second terminal of each first switch SW1 is coupled to a first output terminal (e.g. non-inverting output terminal) of the differential amplifier 620. A first terminal and a second terminal of the second switch SW2 are respectively coupled to the first input terminal and the first output terminal of the differential amplifier 620. A first terminal and a second terminal of the third switch SW3 are respectively coupled to a second terminal of each first switch SW1 and the common mode voltage VCM. A first terminal and a second terminal of the fourth switch SW4 are respectively coupled to the second terminal of each first switch SW1 and the first output terminal of the differential amplifier 620.

A first terminal and a second terminal of the second capacitor C2 are respectively coupled to the second input terminal VIN_GA of the amplifier 332 and a second input terminal (e.g. non-inverting input terminal) of the differential amplifier 620. A first terminal and a second terminal of the fifth switch SW5 are respectively coupled to the second input terminal and a second output terminal (e.g. inverting output terminal) of the differential amplifier 620. A first terminal of the fourth capacitor C4 is coupled to the second input terminal of the differential amplifier 620. A first terminal and a second terminal of the sixth switch SW6 are respectively coupled to a second terminal of the fourth capacitor C4 and the common mode voltage VCM. A first terminal and a second terminal of the seventh switch SW7 are respectively coupled to the second terminal of the fourth capacitor C4 and the second output terminal of the differential amplifier 620.

During the first period T1 of the sensing period, the second switch SW2, the third switch SW3, the fifth switch SW5 and the sixth switch SW6 are turned on, and the fourth switch SW4 and the seventh switch SW7 are turned off. During the second period T2 of the sensing period, the second switch SW2, the third switch SW3, the fifth switch SW5 and the sixth switch SW6 are turned off, and the fourth switch SW4 and the seventh switch SW7 are turned on. An output voltage of the differential amplifier 620 is written as the following equation (1), in which Voffset denotes a voltage offset of the differential amplifier 620, and A denotes the gain of the differential amplifier 620.

$$V_o = -\left(\frac{A}{1+A}\right)\left(\frac{C1}{C3}\right)(\text{VIP\_GA} - \text{VIN\_GA}) + \left(\frac{A}{1+A}\right)\cdot VCM + \left[\frac{A}{(1+A)^2}\right]\left(\frac{C1}{C3}\right)\cdot VCM + \left[\frac{A}{(1+A)^2}\right]\cdot VCM + \left[\frac{A}{(1+A)^2}\right]\left(\frac{C1}{C3}\right)\cdot V_{offset} + \left[\frac{A}{(1+A)^2}\right]\cdot V_{offset} \quad (1)$$

It should be noted that the capacitance C3 in the equation (1) is provided by the third capacitors C3. If more first switches SW1 are turn on, more third capacitors C3 are connected in parallel, and thus the capacitance C3 in the equation (1) is greater. In contrast, if at least one of the first switches SW1 is turned off, the capacitance C3 in the equation (1) is decreased. Referring to FIG. 3B and FIG. 6, in the embodiment, when the controlling circuit 354 needs to increase the gain of the amplifier 332, the controlling circuit 354 turns off at least one of the first switches SW1. In contrast, when the controlling circuit 354 needs to decrease the gain of the amplifier 332, the controlling circuit 354 turns on at least one of the first switches SW1. In other words, the controlling circuit 354 controls the conducting status of the first switches SW1 to adjust the gain of the amplifier 332.

Figure 7:
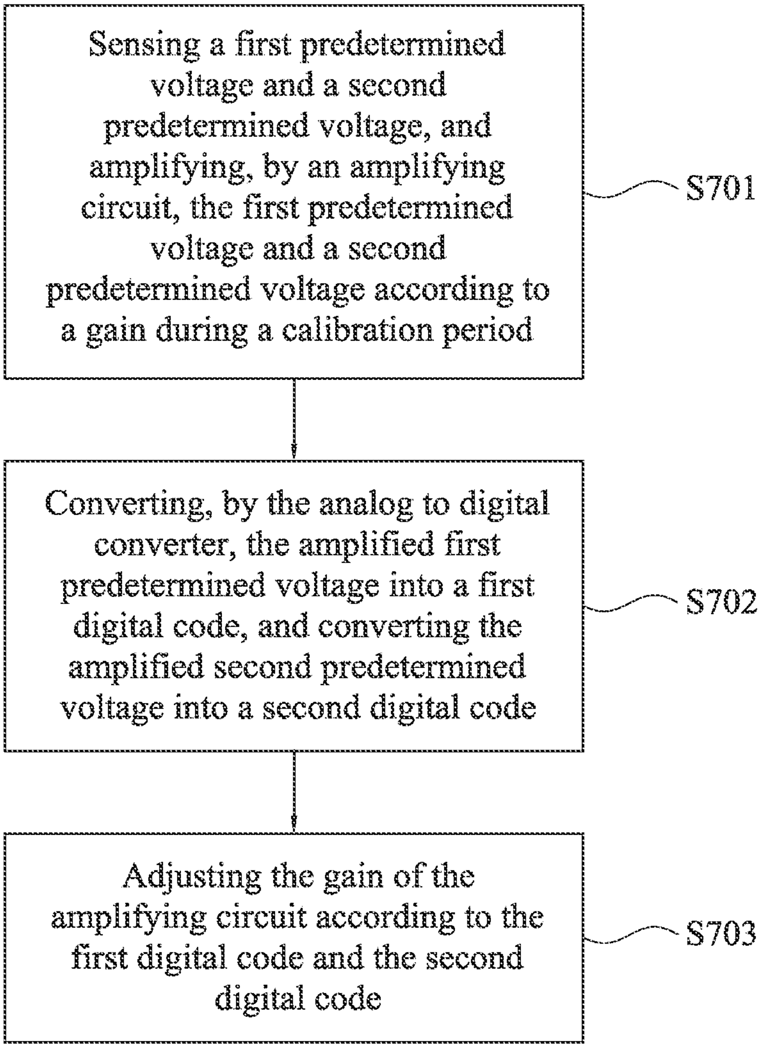
FIG. 7 is a flowchart illustrating a controlling method for a display panel according to an embodiment.

FIG. 7 is a flowchart illustrating a controlling method for a display panel according to an embodiment. Referring to FIG. 7, in a step S701, the first predetermined voltage and the second predetermined voltage are sensed during the calibration period, and the first predetermined voltage and the second predetermined voltage are amplified according to the gain by the amplifying circuit. In a step S702, the first predetermined voltage is converted into the first digital code, and the second predetermined voltage is converted into the second digital code by the analog to digital converter during the calibration period. In a step S703, the gain of the amplifying circuit is adjusted according to the first digital code and the second digital code. Each step in FIG. 7 has been described above, and therefore the description of the steps will not be repeated. It is worth mentioning that each step in FIG. 7 can be implemented as program codes or circuits, which is not limited in the invention. In addition, the method in FIG. 7 can be performed with the said embodiments or performed independently.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A calibrating circuit for a display panel, wherein the display panel comprises a source driver, a gate driver, and a pixel circuit comprising a driving transistor, the calibrating circuit in the source driver comprising:

a pixel sensor having an input terminal coupled to the pixel circuit through a data line of the display panel, for sensing a terminal voltage of the driving transistor during a sensing period, wherein the terminal voltage of the driving transistor is a threshold voltage;

at least one calibration sensor having input terminals coupled to a first predetermined voltage and a second predetermined voltage;

an amplifying circuit having an input terminal coupled to the pixel sensor and the at least one calibration sensor, for amplifying the terminal voltage of the driving transistor according to a gain of the amplifying circuit during the sensing period to obtain an amplified terminal voltage, and amplifying the first predetermined voltage and the second predetermined voltage according to the gain of the amplifying circuit during a calibration period to obtain an amplified first predetermined voltage and an amplified second predetermined voltage respectively;

an analog to digital converter having an input terminal coupled to an output terminal of the amplifying circuit, for converting the amplified terminal voltage into a digital code during the sensing period, and converting the amplified first predetermined voltage into a first digital code and converting the amplified second predetermined voltage into a second digital code during the calibration period; and a gain adjusting circuit coupled to an output terminal of the analog to digital converter and the amplifying circuit, for adjusting the gain of the amplifying circuit according to the first digital code and the second digital code.

2. The calibrating circuit of claim 1, wherein the gain adjusting circuit comprises:

a first register for storing the first digital code;

a second register for storing the second digital code;

a comparing circuit having input terminals coupled to the first register and the second register, for calculating a first difference between the first digital code and the second digital code; and a controlling circuit adjusting the gain of the amplifying circuit according to the first difference.

3. The calibrating circuit of claim 2, wherein if the first difference is less than a predetermined threshold, the controlling circuit increases the gain of the amplifying circuit, if the first difference is greater than the predetermined threshold, the controlling circuit decreases the gain of the amplifying circuit.

4. The calibrating circuit of claim 3, wherein after the controlling circuit adjusts the gain of the amplifying circuit, the amplifying circuit amplifies the first predetermined voltage and the second predetermined voltage according to the adjusted gain, and the analog to digital converter re-generates the first digital code and the second digital code to obtain a re-generated first digital code and a re-generated second digital code respectively, the comparing circuit calculates a second difference between the re-generated first digital code and the re-generated second digital code, if the first difference is less than the predetermined threshold and the second difference is greater than the predetermined threshold, or the first difference is greater than the predetermined threshold and the second difference is less than the predetermined threshold, the controlling circuit stops adjusting the gain of the amplifying circuit, and if the first difference and the second difference are both less than the predetermined threshold or both greater than the predetermined threshold, the controlling circuit continues adjusting the gain of the amplifying circuit.

5. The calibrating circuit of claim 1, wherein the first predetermined voltage is essentially at 25% of an input converting range of the amplifying circuit, and the second predetermined voltage is essentially at 75% of the input converting range.

6. The calibrating circuit of claim 1, wherein the amplifying circuit comprises:

a switch, coupled to the pixel sensor and the at least one calibration sensor; and an amplifier, coupled to the switch, wherein the switch couples the pixel sensor to the amplifier during the sensing period, and couples the at least one calibration sensor to the amplifier during the calibration period, wherein the amplifier comprises:

a differential amplifier having a first input terminal and a second input terminal coupled to a second output terminal of the at least one calibration sensor;

a first capacitor having a first terminal and a second terminal respectively coupled to the first output terminal of the at least one calibration sensor and the first input terminal of the differential amplifier;

a second capacitor having a first terminal and a second terminal respectively coupled to the second output terminal of the at least one calibration sensor and the second input terminal of the differential amplifier;

a plurality of third capacitance adjusting circuits, wherein each of the third capacitance adjusting circuits comprises a third capacitor and a first switch, a first terminal of each of the third capacitor is coupled to the first input terminal of the differential amplifier, a second terminal of each of the third capacitor is coupled to a first terminal of one of the first switch, a second terminal of each of the first switches is coupled to a first output terminal of the differential amplifier;

a second switch having a first terminal and a second terminal respectively coupled to the first input terminal of the differential amplifier and a first output terminal of the differential amplifier;

a third switch having a first terminal coupled to second terminals of the first switches and a second terminal coupled to a common mode voltage;

a fourth switch having a first terminal coupled to the second terminals of the first switches and a second terminal coupled to the first output terminal of the differential amplifier;

a fourth capacitor having a first terminal coupled to the second input terminal of the differential amplifier;

a fifth switch having a first terminal and a second terminal respectively coupled to the second input terminal of the differential amplifier and a second output terminal of the differential amplifier;

a sixth switch having a first terminal and a second terminal respectively coupled to a second terminal of the fourth capacitor and the common mode voltage; and a seventh switch having a first terminal and a second terminal respectively coupled to the second terminal of the fourth capacitor and the second output terminal of the differential amplifier, wherein the gain adjusting circuit controls a conducting status of each of the first switches to adjust the gain of the amplifying circuit.

7. A calibrating method for a display panel comprising a source driver, a gate driver, and a pixel circuit comprising a driving transistor, wherein a terminal voltage of the driving transistor is sensed by a pixel sensor, wherein the terminal voltage of the driving transistor is a threshold voltage, the terminal voltage of the driving transistor is amplified according to a gain of the amplifying circuit by an amplifying circuit to obtain an amplified terminal voltage, and the amplified terminal voltage is converted into a digital code by an analog to digital converter during a sensing period, and wherein the calibrating method is performed by a calibrating circuit in the source driver, the calibrating method comprising:

sensing a first predetermined voltage and a second predetermined voltage, and amplifying, by the amplifying circuit, the first predetermined voltage and the second predetermined voltage according to the gain of the amplifying circuit during a calibration period to obtain an amplified first predetermined voltage and an amplified second predetermined voltage respectively;

converting, by the analog to digital converter, the amplified first predetermined voltage into a first digital code, and converting the amplified second predetermined voltage into a second digital code during the calibration period; and adjusting the gain of the amplifying circuit according to the first digital code and the second digital code.

8. The calibrating method of claim 7, wherein the step of adjusting the gain of the amplifying circuit according to the first digital code and the second digital code comprises:

calculating a first difference between the first digital code and the second digital code;

if the first difference is less than a predetermined threshold, increasing the gain of the amplifying circuit; and if the first difference is greater than the predetermined threshold, decreasing the gain of the amplifying circuit.

9. The calibrating method of claim 8, further comprising:

after adjusting the gain of the amplifying circuit, amplifying, by the amplifying circuit, the first predetermined voltage and the second predetermined voltage according to the adjusted gain, and re-generating, by the analog to digital converter, the first digital code and the second digital code to obtain a re-generated first digital code and a re-generated second digital code respectively;

calculating a second difference between the re-generated first digital code and the re-generated second digital code;

if the first difference is less than the predetermined threshold and the second difference is greater than the predetermined threshold, or the first difference is greater than the predetermined threshold and the second difference is less than the predetermined threshold, stopping adjusting the gain of the amplifying circuit; and if the first difference and the second difference are both less than the predetermined threshold or both greater than the predetermined threshold, continuing adjusting the gain of the amplifying circuit.

10. The calibrating method of claim 9, wherein the first predetermined voltage is essentially at 25% of an input converting range of the amplifying circuit, and the second predetermined voltage is essentially at 75% of the input converting range.

* * * * *